(12) United States Patent
Campbell

(10) Patent No.: US 9,040,636 B2
(45) Date of Patent: May 26, 2015

(54) HYDROXY ESTER RESINS

(71) Applicant: Dow Global Technologies LLC, Midland, MI (US)

(72) Inventor: E. J. Campbell, Missouri City, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/357,380

(22) PCT Filed: Nov. 29, 2012

(86) PCT No.: PCT/US2012/066929
§ 371 (c)(1),
(2) Date: May 9, 2014

(87) PCT Pub. No.: WO2013/090010
PCT Pub. Date: Jun. 20, 2013

(65) Prior Publication Data
US 2014/0316099 A1 Oct. 23, 2014

Related U.S. Application Data

(60) Provisional application No. 61/576,032, filed on Dec. 15, 2011.

(51) Int. Cl.
| | | |
|---|---|---|
| *C08G 63/42* | (2006.01) | |
| *C08G 65/26* | (2006.01) | |
| *C08F 22/20* | (2006.01) | |
| *C07C 67/26* | (2006.01) | |
| *C07C 69/54* | (2006.01) | |
| *C08K 5/10* | (2006.01) | |
| *C08G 59/22* | (2006.01) | |
| *C08L 67/02* | (2006.01) | |

(52) U.S. Cl.
CPC .............. *C08G 65/2615* (2013.01); *C08K 5/10* (2013.01); *C08G 59/22* (2013.01); *C08L 67/02* (2013.01); *C08F 22/20* (2013.01); *C07C 67/26* (2013.01); *C07C 69/54* (2013.01)

(58) Field of Classification Search
CPC ......... C08G 59/22; C08L 63/00; C08L 67/02; C08K 5/10
USPC .......................... 525/411, 412, 418, 436, 439
See application file for complete search history.

(56) References Cited

U.S. PATENT DOCUMENTS

| | | |
|---|---|---|
| 3,066,112 A | 11/1962 | Bowen |
| 3,987,090 A | 10/1976 | Gruber et al. |
| 2012/0220750 A1* | 8/2012 | Marks et al. .................. 528/365 |

FOREIGN PATENT DOCUMENTS

WO    WO 98/56500    12/1998

* cited by examiner

*Primary Examiner* — Gregory Listvoyb
(74) *Attorney, Agent, or Firm* — Joe R. Prieto

(57) ABSTRACT

A hydroxy ester resin composition such as a vinyl ester resin including the reaction product of (a) divinylarene dioxide resin; and (b) at least one ring opening reactant such as at least one monocarboxylic acid for example (meth)acrylic acid, in the presence of (c) at least one non-gelling catalyst such as a Lewis acid catalyst; a process for making the hydroxy ester resin composition; a curable hydroxy ester resin composition such as a curable resin composition made from the hydroxy ester resin composition; a process for curing the curable hydroxy ester resin composition; and a cured product made from the curable hydroxy ester resin composition. The cured product made from the above hydroxy ester resin composition is thermally stable and offers improved properties such as a lower viscosity and a high heat resistance compared to known cured products prepared from known epoxy resins.

19 Claims, No Drawings

US 9,040,636 B2

HYDROXY ESTER RESINS

BACKGROUND OF THE INVENTION

1. Field of the Invention

The present invention relates to hydroxy ester resins; curable compositions prepared from such hydroxy ester resins; and articles prepared from such curable compositions.

2. Description of Background and Related Art

Hydroxy ester resins such as vinyl ester resins are known in the art and are useful in various enduses including as a binder resin for glass, carbon and polymer fiber composites. Typically, binder resins useful for composites and based on vinyl ester resins derived from conventional epoxy resins such as aromatic glycidyl ethers contain as much as 90 wt % of an unsaturated monomer such as styrene in order to obtain a solution having an adequate viscosity (e.g. between 500 mPa-s and 6,500 mPa-s at 25° C.) in order to be able to use the solution in the process of making composites. For example, U.S. Pat. No. 3,066,112 describes the preparation of various vinyl ester resins from conventional epoxy resins and (meth) acrylic acids. However, the conventional epoxy resins used to prepare the vinyl ester resins known in the art have a high viscosity (for example, greater than 5,000 mPa-s at 25° C.), which in turn makes a vinyl ester resin product having the same high viscosity. Thus, the resultant vinyl ester resin product requires dilution, in order to lower the product's viscosity, before the product can be used as a binder resin.

In addition, problems are encountered when prior art vinyl ester resins made from conventional epoxy resins are used to form a curable composition; and when such curable compositions are cured to form a thermoset. For example, when greater than 10 wt % of prior art vinyl ester resins made from conventional epoxy resins are used as a binder resin to form a curable composition; and when such curable composition is cured to form a thermoset, the resulting thermoset does exhibit a sufficiently high heat resistance as required for some enduses such as for making composites. A cured composite known in the prior art that has a high heat resistance in terms of glass transition temperature (Tg) is a cured composite that exhibits, for example, a Tg greater than about 140° C.

Also, while some known vinyl ester resins based on conventional aliphatic epoxy resins can have a viscosity of less than 5,000 mPa-s at 25° C., the resulting cured composite made from curing these known vinyl ester resins do not maintain a high heat resistance after curing (e.g., Tg greater than about 140° C.).

It is also known that hydroxy esters of carboxylic acids such as acrylic acid and methacrylic acid can be prepared by reacting acrylic acid or methacrylic acid with 1,2-alkylene oxides in the presence of a nitrogen-containing base which serves as a catalyst in the reaction. For example, U.S. Pat. No. 3,987,090 ("the '090 patent") discloses the preparation of hydroxy esters of acrylic and methacrylic acids and 1,2-alkylene oxides; and an inhibitor $R—NO_2$ (nitrite, $R—O—N=O$) is used to stabilize the acrylic and methacrylic acids. The '090 patent also describes reactions carried out at elevated reaction temperatures (for example, 80° C.-120° C.) in order to obtain reasonable rates of reaction (epoxide conversion greater than 90% after 8 hours). However, when this known reaction is carried out at the above elevated temperatures a so-called "popcorn" polymerization of the acrylic or methacrylic acids occurs (e.g., undesirable yields of insoluble (meth)acrylic acid polymer are formed) resulting in (i) a significant loss of starting material (e.g., 30% to 100% loss of acrylic or methacrylic acids), and (ii) the undesirable production of an insoluble polymer that may clog a reactor utilized for carrying out the reaction.

It is also reported in the '090 patent that the "popcorn" polymerization problem can be avoided to a large extent by utilizing lower reaction temperatures (e.g., 45° C. to 80° C.). However, as reported in the '090 patent, when the above reaction is carried out at lower reaction temperatures, the rates of reaction are so slow (less than 90% epoxide conversion after 24 hours to 36 hours); the process is not economically feasible.

WO 9856500 discloses the use of C3-C60, substituted or unsubstituted, straight or branch-chained, alkyl, aryl, or aralkyl carboxylate Cr(III) salts, preferably Cr(III) octoate, as catalysts for the reaction of ring systems, such as aziridines, oxiranes, oxetanes and thiiranes with carboxylic acids, anhydrides, lactone and carbonate esters. The reactions described in WO 9856500 are performed at 70° C. to 100° C., and at catalyst concentrations in the range of 4 wt % to 10 wt %. In the case of acrylic and methacrylic acid derivatives, when the Cr(III) catalyst is used, as described in WO 9856500, the catalyst adversely reacts with the olefinic starting material and polymerizes the reactant.

SUMMARY OF THE INVENTION

One embodiment of the present invention is directed to a hydroxy ester resin such as a vinyl ester resin including a reaction product of: (a) at least one divinylarene dioxide such as for example a divinylbenzene dioxide (DVBDO); or a blend of (i) a divinylarene dioxide resin and (ii) another epoxy resin other than a divinylarene dioxide; and (b) at least one ring opening reactant for example at least one organic acid such as at least one monocarboxylic acid in the presence of (c) a non-gelling catalyst such as sterically hindered amines or supported amine catalysts or Lewis acid catalysts such as a metal triflate catalysts.

Other embodiments of the present invention are directed to a hydroxy ester resin such as a vinyl ester resin having a low viscosity (e.g., less than about 5,000 mPa-s at 25° C.); and a curable formulation made from such low viscosity hydroxy ester resin which, in turn, can be cured to form a thermoset.

The hydroxy ester resin product of the present invention may beneficially have a reduced viscosity as compared to a hydroxy ester resin prepared from a conventional epoxy resin such that a thermoset prepared from the hydroxy ester resin product of the present invention has a similar Tg to a thermoset prepared from a conventional epoxy resin. Alternatively, the hydroxy ester resin product of the present invention may beneficially have a similar viscosity as compared to a hydroxy ester resin prepared from a conventional epoxy resin such that a thermoset prepared from the hydroxy ester resin product of the present invention has a higher Tg compared to a thermoset prepared from a conventional epoxy resin.

The present invention provides a convenient and commercially-scalable synthesis of methyl acrylic and acrylic acid derivatives of divinylarene dioxides such as DVBDO-DM or DVBDO-DA with high rates of reaction (e.g., epoxide conversion greater than 90% after 20 minutes to 360 minutes) at low reaction temperatures (e.g., 25° C. to 75° C.); and a synthesis that substantially eliminates unwanted polymerization of acrylic and methacrylic acids. For example, in one embodiment of the process of the present invention, the process is run at room temperature (about 25° C.); the non-gelling catalyst of the present invention is used in the process at a concentration in the range of about 50 ppm to about 2000 ppm; and the non-gelling catalyst of the present invention does not adversely react with olefinic starting materials.

Other embodiments of the present invention are directed to a curable resin system derived from the hydroxy ester resin of the present invention; and a process for preparing the curable resin system. For example, in one embodiment, the curable resin system may comprise (i) the hydroxy ester resin composition described above, and (ii) at least one initiator. The curable epoxy resin system may also optionally include another epoxy resin other than and different from the aforementioned at least one divinylarene dioxide, such as for example diglycidyl ether of bisphenol A, diglycidyl ether of bisphenol F, a cycloaliphatic epoxy, or mixtures thereof. The epoxy resins of the present invention may be used with a reactive diluent, a non-reactive diluent or mixtures thereof.

Other embodiments of the present invention include a process for making the above curable resin system; and a process for curing the curable resin system.

DETAILED DESCRIPTION OF THE INVENTION

"Sterically hindered amine" used herein means $NR_3$ where R is $^tBu$, $^iPr$ heterogeneous support, other sufficiently bulky groups familiar to someone skilled in the art; or mixtures thereof.

"Curable" used herein in reference to a composition, means a product that under UV light or heat will cure or polymerize with other olefin groups.

"Metal triflate" used herein in reference to a catalyst, means a metal trifluromethanesulfonate compound.

"High heat resistance" used herein means a Tg greater than about 140° C.

In its broadest scope, the present invention includes a hydroxy ester resin comprising a reaction product of: (a) at least one divinylarene dioxide; (b) at least one monocarboxylic acid; in the presence of (c) at least one non-gelling catalyst; and (d) optionally, an unsaturated monomer. For example, the hydroxy ester resin reaction product may comprise a vinyl ester resin; and the vinyl ester resin may be used to form a curable resin composition or formulation; wherein the resulting curable resin composition or formulation may include one or more optional additives known in the art.

The curable hydroxy ester resin compositions of the present invention advantageously have a low viscosity (e.g., less than about 500 mPa-s at 25° C.) and are suitable for preparing thermosets such as composites. For example, the thermosets of the present invention such as composites may be formed by curing the above curable hydroxy ester resin composition containing a reinforcement material such as glass, carbon, or polymer fiber. The cured composite of the present invention advantageously maintains a high heat resistance.

The reaction scheme for preparing the hydroxy ester resin composition of the present invention involves the catalyzed ring opening of an aryl epoxide such as a divinylarene dioxide with an organic acid compound such as an acrylic acid or a methacrylic acid. The reaction scheme can be illustrated for example by the following reaction Scheme 1:

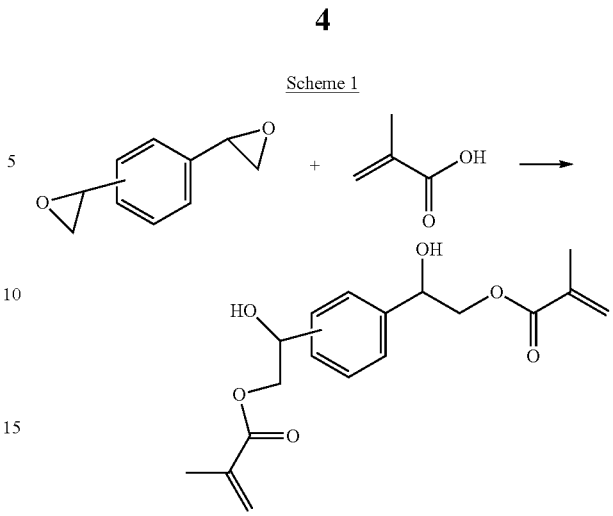

Scheme 1

Generally, the hydroxy ester resins such as vinyl ester resins of the present invention have a lower viscosity than those based on conventional epoxy resins such as aromatic glycidyl ethers and the hydroxy ester resins of the present invention maintain a high heat resistance after curing the resin. For example, the hydroxy ester resin of the present invention has a viscosity effective to allow the hydroxy ester resin composition to become flowable at room temperature (25° C.). Because the hydroxy ester resin of the present invention has a lower viscosity (e.g., about 20 mPa-s at 25° C.) than conventional epoxy resins, the hydroxy ester resin composition of the present invention requires little (less than about 5-10 wt %) dilution with unsaturated monomers such as styrene while maintaining the required heat resistance after curing.

In preparing the hydroxy ester resin reaction product of the present invention, an aryl epoxide or alkylene oxide may be used in the reaction process for making the hydroxy ester resin of the present invention. The aryl epoxide or alkylene oxide may include for example at least one 1,2-alkylene oxide. In one embodiment, the alkylene oxide may include for example 1,2-alkene/aryl monoepoxides and diepoxides. In one preferred embodiment, that at least one 1,2-alkylene oxide can be for example (i) at least one divinylarene dioxide; or (ii) a divinylarene dioxide blended with another epoxy resin other than the divinylarene dioxide. A divinylarene dioxide useful in the present invention may be for example a divinylbenzene dioxide (DVBDO).

The divinylarene dioxides useful in the present invention, particularly those derived from divinylbenzene such as for example DVBDO, are class of diepoxides which have a relatively low liquid viscosity but impart a high heat resistance in its derived thermosets than do conventional epoxy resins. Divinylarene dioxides, for example DVBDO, can be used as either a reactive diluent or a main epoxy resin matrix. DVBDO itself has a very low liquid viscosity making DVBDO especially useful in the preparation of low viscosity epoxy resin formulations.

The divinylarene dioxide useful in the present invention may comprise, for example, any substituted or unsubstituted arene nucleus bearing two vinyl groups in any ring position. The arene portion of the divinylarene dioxide may consist of benzene, substituted benzenes, (substituted) ring-annulated benzenes or homologously bonded (substituted) benzenes, or mixtures thereof. The divinylbenzene portion of the divinylarene dioxide may be ortho, meta, or para isomers or any mixture thereof. Additional substituents may consist of $H_2O_2$-resistant groups including saturated alkyl, aryl, halogen, nitro, isocyanate, or RO— (where R may be a saturated alkyl or aryl). Ring-annulated benzenes may consist of naphthlalene, tetrahydronaphthalene, and the like. Homologously bonded (substituted) benzenes may consist of biphenyl, diphenylether, and the like.

The divinylarene dioxide useful in the present invention may be illustrated by general chemical Structures I-IV as follows:

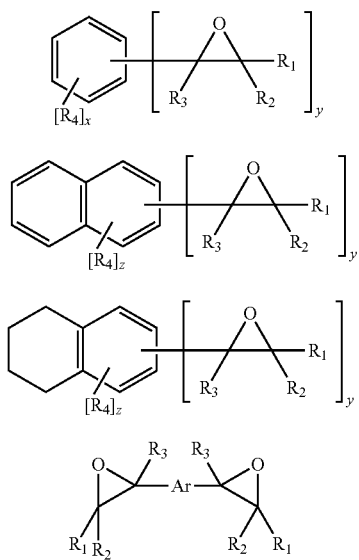

Structure I

Structure II

Structure III

Structure IV

In the above Structures I-IV of the divinylarene dioxide comonomer of the present invention, each $R_1$, $R_2$, $R_3$ and $R_4$ individually may be hydrogen, an alkyl, cycloalkyl, an aryl or an aralkyl group; or a $H_2O_2$-resistant group including for example a halogen, a nitro, an isocyanate, or an RO group, wherein R may be an alkyl, aryl or aralkyl; x may be an integer of 0 to 4; y may be an integer greater than or equal to 2; x+y may be an integer less than or equal to 6; z may be an integer of 0 to 6; and z+y may be an integer less than or equal to 8; and Ar is an arene fragment including for example, 1,3-phenylene group.

In another embodiment, the divinylarene dioxide useful in the present invention may comprise, for example, divinylbenzene dioxide, divinylnaphthalene dioxide, divinylbiphenyl dioxide, divinyldiphenylether dioxide, and mixtures thereof.

In another embodiment, the divinylarene dioxide useful in the present invention may be for example DVBDO. In yet another embodiment, the divinylarene dioxide component useful in the present invention includes, for example, a divinylbenzene dioxide as illustrated by the following chemical formula of Structure V:

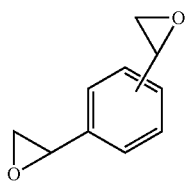

Structure V

The chemical formula of the above DVBDO compound may be as follows: $C_{10}H_{10}O_2$; the molecular weight of the DVBDO is about 162.2; and the elemental analysis of the DVBDO is about: C, 74.06; H, 6.21; and O, 19.73 with an epoxide equivalent weight of about 81 g/mol.

Divinylarene dioxides, particularly those derived from divinylbenzene such as for example DVBDO, are class of diepoxides which advantageously have a relatively low liquid viscosity but a higher rigidity and crosslink density than conventional epoxy resins.

Structure VI below illustrates one preferred embodiment of a chemical structure of the DVBDO useful in the present invention:

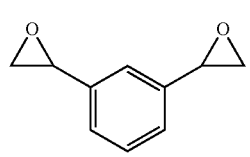

Structure VI

Structure VII below illustrates another preferred embodiment of a chemical structure of the DVBDO useful in the present invention:

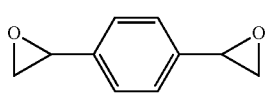

Structure VII

When DVBDO is prepared by the processes known in the art, it is possible to obtain one of three possible isomers: ortho, meta, and para. Accordingly, the present invention includes a DVBDO illustrated by any one of the above structures individually or as a mixture thereof. Structures VI and VII above show the meta (1,3-DVBDO) isomer and the para (1,4-DVBDO) isomer of DVBDO, respectively. The ortho isomer is rare; and usually DVBDO is mostly produced in a general range of from about 9:1 to about 1:9 ratio of meta (Structure VI) to para (Structure VII) isomers in one embodiment. The present invention includes, as another embodiment, a range of from about 6:1 to about 1:6 ratio of Structure VI to Structure VII; a ratio of Structure VI to Structure VII of from about 4:1 to about 1:4 in still another embodiment; and from about 2:1 to about 1:2 in yet another embodiment.

In one embodiment, the divinylarene dioxide, for example DVBDO, useful in the present invention comprises a low viscosity liquid divinylarene dioxide composition. The viscosity of the divinylarene dioxide used in the process for making the vinyl ester resin of the present invention ranges generally from about 10 centipoise (cP) to about 100 cP in one embodiment, from about 10 cP to about 50 cP in another embodiment, and from about 10 cP to about 25 cP at 25° C. in still another embodiment.

The concentration of the divinylarene dioxide used to prepare the epoxy vinyl ester resin of the present invention may range generally from about a molar ratio of divinylarene dioxide to monocarboxylic acid of from about 99:1 to about 1:99 in one embodiment; from about 90:1 to about 1:90 in another embodiment; from about 50:1 to about 1:50 in still another embodiment; and from about 10:1 to about 1:10 in yet another embodiment. In one illustration of the present invention, in order to convert all of the epoxy functionalities of the divinylarene dioxide to vinyl ester functionalities, a preferred embodiment is to use a molar ratio of divinylarene dioxide to monocarboxylic acid of about 1:2.1.

The ring opening reactant used in the process for making a hydroxy ester resin reaction product of the present invention includes for example at least one compound selected from the group consisting of organic acids, amines, alcohols, phenols oxazolidones, phosphines, and mixtures thereof.

In one preferred embodiment, the organic acids may include for example at least one carboxylic acid such as a mono-carboxylic acid. For example, suitable mono-carboxylic acids for reaction with the divinylarene dioxide compounds include acrylic acid, methacrylic acid, cyanoacrylic acid, crotonic acid, alpha-phenylacrylic acid, methoxyacrylic acid, alpha-4-phenylphenylacrylic acid, monomethylester of maleic acid, monomethylester of fumaric acid,

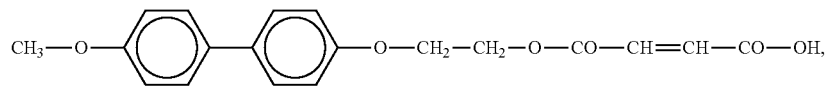

and mixtures thereof. Suitable monocarboxylic acid compounds useful in the present invention are also described for example in U.S. Pat. No. 5,164,464; incorporated herein by reference.

In one preferred embodiment of the present invention, a vinyl ester resin composition can be prepared for example by using a monocarboxylic acid compound including for example methacrylic acid, acrylic acid, acetic acid, or mixtures thereof.

In general, a mole ratio of 2 to 1 of the carboxylic acid group per epoxide group in the divinylarene dioxide compound is used in the present invention in one embodiment, and a ratio of 1.1 to 1 in another embodiment.

In one preferred embodiment, from about 2 equivalents to about 3 equivalents methacrylic acid are used with 1.1 equivalents of amine, and 1 equivalent DVBDO, optionally in a solvent such as toluene at from 0 to about 75 wt %.

The reaction for producing the hydroxy ester resin reaction product of the present invention includes carrying out the reaction in the presence of (c) a non-gelling catalyst. For example, the non-gelling catalyst may include a Lewis acid catalyst, a hindered amine, or mixtures thereof.

In one embodiment, the Lewis acid catalyst may include for example, at least one homogeneous or heterogeneous Lewis Acid catalyst such as for example a sulfate, a sulfonate, a halide (e.g. fluoride, chloride and bromide), or an alkoxide of: aluminum, lanthanum, lithium, calcium, magnesium, barium, copper, or silver; or mixtures thereof. In one preferred embodiment, at least one metal triflate compound is used as the non-gelling catalyst.

In another embodiment, the hindered amine catalyst used to assist in the reaction between the epoxide group of the divinylarene dioxide compound and the carboxylic acid group of the ring opening reactant compound, may include for example one or more aliphatic amines, aromatic amines, and mixtures thereof. For example, in one embodiment, the aliphatic amine may include, but is not limited to, for example diisopropylamine, ditertbutyl amine, or mixtures thereof. In another embodiment, the aromatic amine may include, but is not limited to, for example 2,6-diisopropylpyridine, 2,6-di ditertbutyl pyridine, or mixtures thereof. In still another embodiment, the catalyst may include, but is not limited to, a heterogeneous (supported) amine catalyst such as for example polyvinylpyridine, a basic ion exchange resin, or combinations thereof.

When a Lewis acid is used as the non-gelling catalyst, the concentration of the Lewis Acid catalyst may range generally in a concentration of from about 10 ppm to about 20,000 ppm in one embodiment; from about 50 ppm to about 10,000 ppm in another embodiment; from about 50 ppm to about 5,000 ppm in still another embodiment; and from about 100 ppm to about 1,000 ppm in yet another embodiment.

When a hindered amine catalyst is used as the non-gelling catalyst, the concentration of the hindered amine catalyst may range generally in a concentration of from about 10 ppm to about 20,000 ppm; from about 50 ppm to about 10,000 ppm in another embodiment; and from about 100 ppm to about 1,000 ppm in still another embodiment.

In preparing the hydroxy ester resin reaction product of the present invention, at least one inhibitor may optionally be used in the reaction between the epoxide group of the divinylarene dioxide compound and the carboxylic acid group of the ring opening reactant compound. The inhibitor compound is used to prevent gellation of the reaction composition (e.g., homopolymerization of the hydroxy ester(s) and/or copolymerization of the hydroxy ester(s) such as vinyl ester(s) with unreacted ring opening reactant compound such as monocarboxylic acid); and to prevent the decomposition of any vinyl monocarboxylic acid that may be present in the reaction composition.

For example, the inhibitor used in the present invention may include, conventional inhibitors known in the art such as hydroquinone, isopentylnitrite, commercially available inhibitors such as Prostab™ 5415 available from BASF; and mixtures thereof.

Generally, the inhibitor used in the present invention may be used at concentrations of for example from 0 ppm to less than about 1000 ppm in one embodiment; from about 50 ppm to about 1000 ppm in another embodiment, from about 100 ppm to about 500 ppm in still another embodiment, and from about 100 ppm to about 200 ppm in yet another embodiment, based on the weight of the total reactants used.

The reaction to produce the hydroxy ester resin reaction product of the present invention may optionally be conducted in one or more organic solvents inert to the other reactants. The optional solvent used to facilitate the reaction of the divinylarene dioxide compound with the at least one ring opening reactant such as for example (meth)acrylic acid compound, may include for example, one or more conventional organic solvents well known in the art may. For example, aromatic hydrocarbons such as toluene or xylene; ketones such as methyl ether ketone; ethers such as diglyme; chlorinated aliphatics such as perchloroethylene; and mixtures thereof, may be used in the present invention. The term "inert" as applied to the organic solvent means that little, if any, reaction between the divinylarene dioxide compound, the monocarboxylic acid or the vinyl esters thereof occurs under the reaction conditions employed.

In another embodiment, the optional solvent may include a reactive diluent that is unreactive when formulated into the composition and then can subsequently react when curing the composition. For example, the reactive diluent may include styrene; divinylbenzene monooxide (DVBMO); any unsaturated monomer such as butylacrylate; and mixtures thereof.

The concentration of the optional solvent used in the present invention may range generally from 0 wt % to about 90 wt % in one embodiment, from about 0.01 wt % to about 80 wt % in another embodiment, from about 1 wt % to about 70 wt % in still another embodiment, and from about 10 wt % to about 60 wt % in yet another embodiment, based on the weight of the total reactants used.

In preparing the hydroxy ester resin reaction product of the present invention, at least one unsaturated monomer (also referred to herein as a co-monomer) may optionally be used to dissolve the ring opening reactant such as (meth)acrylic acid therein and to facilitate the reaction between the divinylarene dioxide and the at least one (meth)acrylic acid. For example, the unsaturated monomer may include an ethylenically unsaturated monomer.

Suitable ethylenically unsaturated monomers as co-monomers which can be employed in the present invention can be selected from the many known classes of polymerizable vinyl monomers (vinyl co-monomers). Such suitable polymerizable vinyl monomers include, for example, the vinyl aromatic compounds which include such monomers as styrene, alpha-methylstyrene, vinyl toluenes, halogenated styrenes, t-butylstyrenes, divinylbenzenes or mixtures thereof.

Other suitable unsaturated monomers useful in the present invention include for example the methyl, ethyl, isopropyl, butyl, octyl, etc. esters of acrylic or methacrylic acid; multifunctional esters of ethylene glycol, glycerol, propylene glycol, 1,3-propanediol, butylene glycol, 1,4-butanediol, neopentylglycol, trimethylolpropane, pentaerythritol, and 1,6-hexanediol and the like with acrylic or methacrylic acid; acidic monomers such as acrylic acid, methacrylic acid and crotonic acid; amide monomers such as acrylamide and N-alkylacrylamides; allyl monomers such as diallylphthalate, triallylisocyanurate, diallylmaleate and dimethallylfumarate; mixtures thereof and the like.

In one preferred embodiment, the polymerizable monomers containing ethylenic unsaturation include, for example, styrene; p-vinyltoluene; o-, m- and p-halostyrenes; vinyl naphthalenes; vinyl acetate; the various alpha-substituted styrenes; the various di-, tri- and tetra-halo styrenes; acrylic, methacrylic and crotonic acid esters including both the saturated alcohol esters and the hydroxyalkyl esters; and mixtures thereof.

In another preferred embodiment, the unsaturated monomer useful in the present invention may include, for example, styrene, methyl methacrylate, butyl acrylate, and mixtures thereof.

The concentration of the unsaturated monomer (i.e., the vinyl co-monomer), when used to prepare the vinyl ester resin of the present invention, may range generally from 0 wt % to about 99 wt % in one embodiment; from about 1 wt % to about 99 wt % in another embodiment; from about 1 wt % to about 95 wt % in still another embodiment; from about 5 wt % to about 90 wt % in yet another embodiment; and from about 10 wt % to about 85 wt % in even still another embodiment.

The divinylarene dioxide used in the present invention may be used as the sole epoxy resin component in the reaction composition for preparing the reaction product of the present invention; or the divinylarene dioxide may be used in combination with other epoxy resins known in the art such as epoxy resins described in Lee, H. and Neville, K., *Handbook of Epoxy Resins*, McGraw-Hill Book Company, New York, 1967, Chapter 2, pages 2-1 to 2-27.

Suitable epoxy resins other than the divinylarene dioxide useful in the present invention may include for example epoxy resins based on reaction products of polyfunctional alcohols, phenols, cycloaliphatic carboxylic acids, aromatic amines, or aminophenols with epichlorohydrin. A few non-limiting embodiments include, for example, bisphenol A diglycidyl ether, bisphenol F diglycidyl ether, resorcinol diglycidyl ether, and triglycidyl ethers of para-aminophenols. Other suitable epoxy resins known in the art include for example reaction products of epichlorohydrin with o-cresol and, respectively, phenol novolacs. It is also possible to use a mixture of two or more other epoxy resins with the divinylarene dioxide. The other epoxy resin may also be selected from commercially available products such as for example, D.E.R. 331®, D.E.R. 332, D.E.R. 334, D.E.R. 580, D.E.N. 431, D.E.N. 438, D.E.R. 736, or D.E.R. 732 epoxy resins available from The Dow Chemical Company.

In a preferred embodiment, the reaction composition of the present invention may include, as an optional second epoxy resin other than the divinylarene dioxide, such as for example diglycidyl ether of bisphenol A, diglycidyl ether of bisphenol F or cycloaliphatic epoxies or resins with reactive and non-reactive diluents.

In general, the reaction mixture to prepare the reaction product may include from about 0 wt % to about 99 wt % of the optional second epoxy resin in one embodiment, from about 5 wt % to about 70 wt % second epoxy resin in another embodiment; and from about 10 wt % to about 50 wt % second epoxy resin in still another embodiment.

The preparation of the hydroxy ester resin reaction product of the present invention such as a vinyl ester resin may be achieved by adding to a reactor: at least one ring opening reactant such as a (meth)acrylic acid; a catalyst, and any optional compounds such as a solvent; and then the components are heated to a desired temperature. A divinylarene dioxide is then added dropwise to the reaction mixture in the reactor while vigorously stifling the solution allowing the components to react under reaction conditions until the desired degree of reaction is achieved to produce the epoxy resin composition product. The resulting reaction product is allowed to cool prior to or during isolation and filtered. Thereafter, the reaction product is immediately usable in thermoset compositions or formulations.

The reaction conditions to form the hydroxy ester resin reaction product include carrying out the reaction under a temperature, generally in the range of from about 23° C. to about 110° C. in one embodiment; from about 35° C. to about 85° C. in another embodiment; and from about 45° C. to about 70° C. in still another embodiment.

The pressure of the reaction may be generally from about 0.1 bar to about 10 bar in one embodiment; from about 0.5 bar to about 5 bar in another embodiment; and from about 0.9 bar to about 1.1 bar in still another embodiment.

The reaction to produce the hydroxy ester resin is generally conducted at a reaction time from about 0.1 minutes to about 12 hours in one embodiment, from about 1 minute to about 10 hours in another embodiment, from about 5 minutes to about 8 hours in still another embodiment, from about 20 minutes to about 6 hours in yet another embodiment, and from about 30 minutes to about 60 minutes in even yet another embodiment.

Although reaction times and reaction temperatures can vary in producing the reaction product of the present invention, the hydroxy ester resin may be produced by reacting the reactants to a specific conversion such as for example to a conversion of from about 1.5 wt % to about 0.25 wt % carboxylic acid.

The reaction process to prepare the hydroxy ester resin of the present invention may be a batch or a continuous. The reactor used in the process may be any reactor and ancillary equipment well known to those skilled in the art.

The reaction of a divinylarene dioxide and ring opening reactant such as (meth)acrylic acid in the presence of a catalyst produces the resultant hydroxy ester resin reaction product of the present invention. The reaction product has a lower viscosity and thermosets derived from such products have a higher heat resistance as compared to similar thermoset resins prepared from epoxy resins of the prior art. For example, the viscosity of the hydroxy ester resin composition product prepared by the process of the present invention ranges generally from about 100 cP to about 200,000 cP in one embodiment; from about 150 cP to about 100,000 cP in another embodiment; and from about 200 cP to about 50,000 cP at 150° C. in still another embodiment.

The number average molecular weight ($M_n$) of the hydroxy ester resin product prepared by the process of the present invention ranges generally from about 200 to about 100,000 in one embodiment; from about 300 to about 10,000 in another embodiment; and from about 500 to about 5,000 in still another embodiment.

In one embodiment, the hydroxy ester resin product of the present invention such as a vinyl ester resin may be useful as one component in a UV-thermosettable or UV-curable resin formulation or composition as described herein.

In another broad aspect of the present invention, a curable resin composition may include a hydroxy ester resin reaction product such as the vinyl ester resin reaction product as described above. In one embodiment for example, the hydroxy ester resin of the present invention may be used "as is", i.e., alone without addition of any other optional compounds in the curable composition. For example, when the curable hydroxy ester resin is used alone, it may be cured by heat, i.e. thermally.

In still another embodiment, the hydroxy ester resin of the present invention may be combined with optional components to prepare a curable resin composition such as for example a compound adapted to cure the hydroxy ester resin such as for example a curing agent; an initiator such as a photoinitiator for a UV-curable resin composition; or a curing catalyst to promote the curing reaction.

In one preferred embodiment, the curable hydroxy ester resin composition may comprise a mixture of: the above described hydroxy ester resin reaction product and an optional compound such as for example an unsaturated comonomer different from the vinyl ester resin.

As an illustration of one preferred embodiment of the present invention, for example, a curable vinyl ester resin composition may comprise a reaction mixture of (i) a vinyl ester resin reaction product of a divinylarene dioxide and (meth)acrylic acid as described above, (ii) at least one curing agent; (iii) optionally, at least one curing catalyst; and (iv) optionally, at least one other epoxy resin different from component (i).

The curable hydroxy ester resin composition may comprise for example a hydroxy ester resin as described above, for example a vinyl ester resin.

The concentration of the hydroxy ester resin used in the curable hydroxy ester resin mixture of the present invention may range generally from about 1 wt % to about 100 wt % in one embodiment; from about 5 wt % to about 99 wt % in another embodiment; and from about 10 wt % to about 90 wt % in still another embodiment. Generally, the amount of hydroxy ester resin used is determined based on the properties desired in the derived cured composite.

As aforementioned, the hydroxy ester resin of the present invention may be used "as is" or combined with optional components to prepare a curable resin composition. For example, the optional compounds that may be used in the curable resin composition may comprise curing agents, curing catalysts, initiators, inhibitors, comonomers, adhesion promoters, surfactants, toughening agents, fillers, solvents, other additives known in the art, and mixtures thereof.

In preparing the curable hydroxy ester resin composition mixture of the present invention, in addition to the hydroxy ester resin described above, the mixture may include at least one other epoxy resin, as described above with reference to preparing the hydroxy ester resin reaction product. For example, the epoxy resins described in Lee, H. and Neville, K., "Handbook of Epoxy Resins," McGraw-Hill Book Company, New York, 1967, Chapter 2, pages 257-307; incorporated herein by reference, may be used.

The concentration of the optional epoxy when used in the present invention may range generally from 1 wt % to about 100 wt % in one embodiment, from about 5 wt % to about 75 wt % in another embodiment, from about 10 wt % to about 60 wt % in still another embodiment, and from about 15 wt % to about 45 wt % in yet another embodiment.

In still another embodiment of the present invention, one or more optional organic solvents well known in the art may be used in the curable resin composition. For example, aromatics such as xylene, ketones such as methyl ether ketone, and alcohols such as 1-methoxy-2-propanol; and mixtures thereof, may be used in the present invention. Any of the solvent described above with reference to preparing the hydroxy ester resin reaction product may also be used.

The concentration of the optional solvent used in the present invention may range generally from 0 wt % to about 90 wt % in one embodiment, from about 1 wt % to about 80 wt % in another embodiment, from about 10 wt % to about 65 wt % in still another embodiment, and from about 20 wt % to about 50 wt % in yet another embodiment.

The curable or thermosettable resin composition of the present invention may optionally contain an assortment of one or more other additives useful for the preparation, storage, and curing of the curable vinyl ester resins. For example, the optional additives useful in the present invention composition may include, but are not limited to, catalysts, curing catalysts, solvents, other resins, stabilizers, fillers, inert fillers, plasticizers, catalyst de-activators, inhibitors, curing inhibitors, initiators, curing initiators, surfactants, flow modifiers, impact modifiers, pigments, colorants, dyes, matting agents, degassing agents, toughening agents, wetting agents, flame retardants (e.g., inorganic flame retardants, halogenated flame retardants, and non-halogenated flame retardants such as phosphorus-containing materials), thermoplastics, thermoplastic particles, processing aids, UV blocking compounds, fluorescent compounds, UV stabilizers, fibrous reinforcements, antioxidants, and mixtures thereof. The above list is intended to be exemplary and not limiting. The preferred additives for the formulation of the present invention may be optimized by the skilled artisan.

The concentration of the additional additives may be generally between about 0 wt % to about 90 wt % in one embodiment; between about 0.01 wt % to about 80 wt % in another embodiment; between about 1 wt % to about 65 wt % in still another embodiment; and between about 10 wt % to about 50 wt % in yet another embodiment, based on the weight of the total composition.

As an illustration of one embodiment of a curable resin composition of the present invention, an initiator such as a photoinitiator may be admixed with the hydroxy ester resin reaction product described above to form a UV-curable resin composition. In accordance with this embodiment, the UV-curable resin composition comprises (i) the hydroxy ester resin particularly a vinyl ester resin product as described above; and (ii) at least one photoinitiator.

The preparation of the curable resin composition of the present invention is achieved by admixing in a vessel the following components: the hydroxy ester resin such as a vinyl ester resin, and any optional compounds such as an initiator, a catalyst, another vinyl ester resin, another epoxy resin, or an inert organic solvent; and then allowing the components to formulate into a hydroxy ester resin composition. There is no criticality to the order of mixture, i.e., the components of the formulation or composition of the present invention may be admixed in any order to provide the thermosettable composition of the present invention. Any of the above-mentioned optional assorted formulation additives, for example fillers, may also be added to the composition during the mixing or prior to the mixing to form the composition.

All the components of the curable resin composition are typically mixed and dispersed at a temperature enabling the preparation of an effective resin composition having a low viscosity for the desired application.

The curable resin formulation or composition of the present invention can be cured under conventional processing conditions to form a thermoset. The resulting thermoset displays excellent thermo-mechanical properties, such as good toughness and mechanical strength, while maintaining high thermal stability.

The process to produce the thermoset products of the present invention may be performed by gravity casting, vacuum casting, automatic pressure gelation (APG), vacuum pressure gelation (VPG), infusion, filament winding, lay up injection, transfer molding, prepregging, dipping, coating, spraying, brushing, and the like.

The curing process of the present invention may be a batch or a continuous process. The reactor used in the process may be any reactor and ancillary equipment well known to those skilled in the art.

The cured or thermoset product prepared by curing the curable resin composition of the present invention advantageously exhibits an improved balance of thermo-mechanical properties (e.g. transition temperature, modulus, and toughness).

The heat resistance of the hydroxy ester resin based thermoset of the present invention ranges generally from about 50° C. to about 300° C. in one embodiment; from about 75° C. to about 275° C. in another embodiment; and from about 100° C. to about 250° C. in still another embodiment, as measured by the glass transition temperature (Tg) using differential scanning calorimetry (DSC).

In general, the hydroxy ester resin based compositions of the present invention may be useful in a wide variety of enduse applications including for example castings, coatings, encapsulations, potting, molding, tooling, films, adhesives, laminates, composites, composites, electronics, and the like.

EXAMPLES

The following examples further illustrate the present invention in detail but should not be construed as limiting the scope thereof. In the following Examples, various terms and designations are used such as for example:

"RT" stands for room temperature which herein is about 25° C.

"THF" stands for tetrahydrofuran.

"DVBDO-DM" stands for divinylbenzene dioxide dimethacrylate.

"DGEBA" stands for diglycidyl ether of bisphenol A.

"BDDGE" stands for butane diol diglycidyl ether.

"DSC" stands for differential scanning calorimetry.

In the following Examples, standard analytical equipment and methods are used such as for example:

$^1$H-NMR Measurements $^1$H-NMR measurements are recorded on a Bruker AVANCE NMR instrument (250 MHz for $^1$H). $^1$H NMR data are reported as follows: chemical shift, (multiplicity, integration and peak ID). $^1$H-NMR spectrum are reported in ppm downfield from tetramethylsilane (TMS, δ scale) with solvent resonance as internal standard.

Mass Spectra Measurements

ESI Mass Spectra are obtained using a Waters LCT Premier XE electrospray ionization time-of-flight mass spectrometer (ESI-TOF MS) (Waters, Millford, Mass.). Mass spectra are obtained in the positive ion mode with the capillary (1500 V), cone (ranging from 20 V to 140 V, where needed), source temperature (110° C.), desolvation chamber (250° C.) and TOF mass analyzer potentials optimized to achieve the best signal-to-noise ratio.

In the Examples, the following materials are used.

Prostab 5198 inhibitor is commercially available from BASF. CDCl$_3$ and d-THF are solvents purchased from Cambridge Isotope Laboratories and used as received. DVBDO is synthesized following literature precedent. All other chemicals are purchased from the Aldrich Chemical or Strem Chemical Company and used as received unless otherwise noted.

Example 1

Divinylbenzene dioxide (5.0 grams, 0.031 mol), methacrylic acid (5.6 grams, 2.05 equivalents), toluene (25 mL) and 1,8-bis(dimethylamino)naphthalene, N',N',N',N'-tetramethyl-1,8-naphthalenediamiine (0.05 equivalents) was stirred at 75° C. for six hours (hr). The resulting slurry was allowed to cool to RT and then filtered. The filtrate was washed with 1M NaOH (2×, 20 mL) and H$_2$O (30 mL) and then dried over MgSO$_4$. The solvent was removed under reduced pressure to afford DVBDO-DM, yield=94%. $^1$H-NMR (250 MHz, CDCl$_3$): δ 7.46 (m, 4H, ArH), 5.84 (m, 2H, H$_2$C=C(CH$_3$)—), 5.36 (m, 2H, H$_2$C=C(CH$_3$)—), 4.82 (m, 2H, Ar—CH(OH)—CH$_2$—), 4.59 (m, 2H, Ar—CH(OH)—CH$_2$—), 4.31 (m, 2H, Ar—CH(OH)—CH$_2$—), 1.91 (s, 6H, H$_2$C=C(CH$_3$)—). ESI-MS calculated for C$_{18}$H$_{22}$O$_6$ 334.141. Found 334.141 (Na$^+$).

Example 2

Divinylbenzene dioxide (5.0 grams, 0.031 mol), methacrylic acid (5.6 grams, 2.05 equivalents), toluene (25 mL) and polyvinyl pyridine (0.05 equivalents) was stirred at 75° C. for six hours. The resulting slurry was allowed to cool to RT and then filtered. The filtrate was washed with 1M NaOH (2×, 20 mL) and H$_2$O (30 mL) and then dried over MgSO$_4$. The solvent was removed under reduced pressure to afford DVBDO-DM, yield=91%. ESI-MS calculated for C$_{18}$H$_{22}$O$_6$ 334.141. Found 334.141 (Na$^+$).

Example 3

Divinylbenzene dioxide (5.0 grams, 0.031 mol), methacrylic acid (5.6 grams, 2.05 equivalents), toluene (25 mL) and 2,6-di-tertbutylpyridine (0.05 equivalents) was stirred at 75° C. for six hr and had partially solidified upon discontinuing the heat. The resulting slurry was allowed to cool to RT and then filtered. The filtrate was washed with 1M NaOH (2×, 20 mL) and H$_2$O (30 mL) and then dried over MgSO$_4$. The solvent was removed under reduced pressure to afford DVBDO-DM, yield=61%. ESI-MS calculated for C$_{18}$H$_{22}$O$_6$ 334.141. Found 334.141 (Na$^+$).

Example 4

Divinylbenzene dioxide (5.0 grams, 0.031 mol), methacrylic acid (5.6 grams, 2.05 equivalents), styrene (2.3 grams, 19 wt %) and polyvinyl pyridine (0.05 equivalents) was stirred at 75° C. for six hr. The resulting slurry was allowed to cool to RT and then filtered. The filtrate was washed with 1M NaOH (2×, 20 mL) and H$_2$O (30 mL) and then dried over MgSO$_4$. The resultant reaction product formed was a hydroxy ester resin.

Example 5

Divinylbenzene dioxide (5.0 grams, 0.031 mol), methacrylic acid (5.6 grams, 2.05 equivalents), butyl acrylate (8.3 grams, 40 wt %) and polyvinyl pyridine (0.05 equivalents) was stirred at 75° C. for six hr. The resulting slurry was allowed to cool to RT and then filtered. The filtrate was washed with 1M NaOH (2×, 20 mL) and H$_2$O (30 mL) and then dried over MgSO$_4$. The resolution reaction product formed was a hydroxy ester resin.

Example 6

A mixture of aluminum triflate (2 milligrams (mg)) and methacrylic acid (1.2 grams (g), 0.014 mol) was stirred in a 10 ml beaker at RT for 20 minutes (min). A solution of DVBDO (1.10 g, 0.007 mol) in toluene (4 g) was added drop wise into the beaker over 10 min After complete addition the resulting mixture was stirred at RT for another 20 min and then filtered to remove the aluminum triflate catalyst. The toluene solvent was removed under reduced pressure to afford DVBDO-DM (yield=98%). $^1$H-NMR (250 MHz, CDCl$_3$): δ 7.46 (m, 4H, ArH), 5.84 (m, 2H, H$_2$C=C(CH$_3$)—), 5.36 (m, 2H, H$_2$C=C(CH$_3$)—), 4.82 (m, 2H, Ar—CH(OH)—CH$_2$—), 4.59 (m, 2H, Ar—CH(OH)—CH$_2$—), 4.31 (m, 2H, Ar—CH(OH)—CH$_2$—), 1.91 (s, 6H, H$_2$C=C(CH$_3$)—). ESI-MS calculated for C$_{18}$H$_{22}$O$_6$ 334.141. Found 334.141 (Na$^+$).

Example 7

Aluminum triflate (0.05 g), methacrylic acid (4.1 g, 0.047 mol) THF (33 g) and DGEBA (8.0 g, 0.023 moles) was added into a 100 mL round bottom flask and stirred at reflux temperature for 4 hr. The reaction was allowed to cool to RT and filtered through a 5 micron filter. The THF was removed in vacuo to afford DGEBA-DM (yield=99%). $^1$H-NMR (250 MHz, d-THF): δ 7.05 (d, 4H, ArH), 6.77 (d, 4H, ArH), 6.12 (b, 2H, H$_2$C=C(CH$_3$)—), 5.56 (b, 2H, H$_2$C=C(CH$_3$)—), 3.95-3.37 (m, 10H, Ar—CH$_2$—CH(OH)—CH$_2$—), 1.89 (s, 6H, H$_2$C=C(CH$_3$)—), 1.57 (s, 6H, Ar—C(CH$_3$)$_2$—Ar). ESI-MS calculated for C$_{29}$H$_{36}$O$_8$ 512.24. Found 512.24 (Na$^+$).

Example 8

Aluminum triflate (0.05 g), methacrylic acid (4.1 g, 0.047 moles) toluene (40 g) and BDGGE (4.8 g, 0.023 moles) was added into a 100 mL round bottom flask and stirred at reflux temperature for 4 hr. The reaction was allowed to cool to RT and filtered through a 5 micron filter. The toluene was removed under reduced pressure to afford BDDGE-DM (yield=99%). Calculated for C$_{16}$H$_{26}$O$_8$ 346.37. Found 346.37 (Na$^+$).

Examples 9-15

Methacrylic acid (11.7 wt %), divinylbenzene dioxide (10.2 wt %) in THF (78.1 wt %) was contacted with the Lewis acid (250 ppm) catalysts shown in Table I and stirred at atmospheric pressure and RT for 5 hr. Aliquots of the reactions were diluted with acetonitrile and neutralized using Na$_2$PO$_4$ (aq, 25 wt %), filtered through a 0.22 micron filter and analyzed by gas chromatography (GC) and high pressure liquid chromatography (HPLC) to determine conversion and yield.

TABLE I

Catalytic Ring Opening of DVBDO Using Metallic Lewis Acids

| Example | Catalyst | Yield (%) |
|---|---|---|
| 9 | lanthanum triflate | 100 |
| 10 | calcium triflate | 81.2 |
| 11 | magnesium triflate | 74.5 |
| 12 | barium triflate | 100 |
| 13 | copper triflate | 100 |
| 14 | silver triflate | 69.3 |
| 15 | lithium triflate | 14.2 |

Comparative Examples A-I

The procedure described for Examples 4-10 was repeated using the catalysts shown in Table II. The catalysts described in Table II are not considered "non-gelling catalysts" in accordance with the present invention.

TABLE II

| Example | Catalyst | Yield (%) | Result |
|---|---|---|---|
| A | titanium isopropoxide | — | gelled |
| B | lanthanum phosphate | 0 | — |
| C | calcium methoxide | 6.3 | — |
| D* | calcium methoxide | 21.7 | — |
| E | aluminum ethoxide | — | gelled |
| F | lithium tert-butoxide | 0 | — |
| G | aluminum acetate | 0 | — |
| H | aluminum hexafluro acetonoate | 8.4 | — |
| I | barium isopropoxide | — | gelled |

*Reaction temperature = 45° C.
"—" in Table II above means an appropriate measurement was not capable of being obtained.

Metal triflates are excellent catalysts for the ring opening of DVBDO with carboxylic acid and quantitative conversion was achieved with a variety of metal triflates as shown in Table I. Based upon the comparative examples shown in Table II, metals catalysts with lower Lewis acidity such as metal alkoxides and phosphates have poor activity at room temperature.

Example 16

Aluminum triflate (2 mg) and methacrylic acid (2.2 g, 0.028 mol) and styrene (4.4 g, 50 wt %) was stirred in a 50 ml beaker at RT for 20 minutes. DVBDO (2.20 g, 0.014 mol) was added drop wise into the stirred contents of the beaker over 10 min. After complete addition the resulting mixture was stirred at RT for another 20 min and then filtered to remove the aluminum triflate catalyst. The resultant reaction product formed was a hydroxy ester resin.

The invention claimed is:

1. A hydroxy ester resin comprising the reaction product of (a) at least one divinylarene dioxide, and (b) at least one monocarboxylic acid in the presence of (c) a non-gelling catalyst.

2. The resin of claim 1, wherein the divinylarene dioxide is selected from the group comprising divinylbenzene dioxide, divinylnaphthalene dioxide, divinylbiphenyl dioxide, divinyldiphenylether dioxide, and mixtures thereof.

3. The resin of claim 1, wherein the divinylarene dioxide comprises divinylbenzene dioxide; and wherein the concentration of said divinylbenzene dioxide ranges from about 0.5 weight percent to about 99.5 weight percent.

4. The resin of claim 1, wherein the monocarboxylic acid comprises acrylic acid, methacrylic acid, cyanoacrylic acid, crotonic acid, alpha-phenylacrylic acid, methoxyacrylic acid, alpha-4-phenylphenylacrylic acid, monomethylester of maleic acid, monomethylester of fumaric acid,

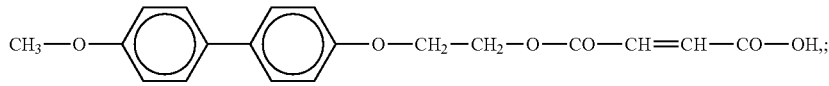

or mixtures thereof.

5. The resin of claim 1, wherein the equivalents of the carboxylic acid per equivalent of epoxide ranges from about 2 to about 0.1.

6. The resin of claim 1, wherein the non-gelling catalyst comprises a Lewis acid catalyst, a hindered amine, a supported amine, or a mixture thereof.

7. The resin of claim 6, wherein the Lewis acid catalyst comprises a triflate.

8. The resin of claim 6, wherein the hindered amine or supported amine catalyst comprises 1,8-bis(dimethylamino) naphthalene; N',N',N',N'-tetramethyl-1,8-naphthalenediamiine; polyvinyl pyridine; 2,6-di-tertbutylpyridine; or mixtures thereof.

9. The resin of claim 1, including further an epoxy resin other than the at least one divinylarene dioxide component (a); wherein the epoxy resin comprises diglycidyl ether of bisphenol A, diglycidyl ether of bisphenol F, a cycloaliphatic epoxy resin, or mixtures thereof.

10. A curable resin composition comprising (a) a hydroxy ester resin composition of claim 1; and (b) an initiator.

11. A curable vinyl ester resin composition comprising (i) at least one hydroxy ester resin of claim 10; and (ii) at least one vinyl comonomer.

12. The curable composition of claim 10, wherein the concentration of said the hydroxy ester resin ranges from about 0.1 weight percent to about 99.9 weight percent.

13. The curable composition of claim 10, including further an inhibitor; wherein the concentration of the inhibitor ranges from about 0.01 weight percent to about 20 weight percent.

14. The curable composition of claim 11, wherein the vinyl comonomer comprises styrene; alpha-methylstyrene; vinyl toluenes; halogenated styrenes; t-butylstyrenes; divinylbenzenes; the methyl, ethyl, isopropyl, butyl, or octyl esters of acrylic or methacrylic acid; multifunctional esters of ethylene glycol, glycerol, propylene glycol, 1,3-propanediol, butylene glycol, 1,4-butanediol, neopentylglycol, trimethylolpropane, pentaerythritol, or 1,6-hexanediol with acrylic or methacrylic acid; acrylic acid; methacrylic acid; crotonic acid; acrylamide; N-alkylacrylamides; diallylphthalate; triallylisocyanurate; diallylmaleate; dimethallylfumarate; or mixtures thereof.

15. A process of preparing a hydroxy ester resin comprising reacting (a) at least one divinylarene dioxide, and (b) at least one monocarboxylic acid in the presence of (c) a non-gelling catalyst.

16. A process of preparing a curable resin composition comprising admixing (a) a hydroxy ester resin composition of claim 1; and (b) an initiator.

17. A process for preparing a vinyl ester resin comprising reacting (a) a divinylarene dioxide, and (b) the monocarboxylic acid; wherein the monocarboxylic acid comprises an acrylic acid, a (meth)acrylic acid, or mixtures thereof, in the presence of (c) a non-gelling catalyst to provide a vinyl ester resin composition.

18. A process for preparing a curable vinyl ester resin composition comprising admixing (i) a hydroxy ester resin composition of claim 1; and (ii) at least one vinyl comonomer; and (iii) optionally, a polymerization inhibitor, or (iv) optionally, a polymerization initiator.

19. An article made from the curable resin of claim 10.

* * * * *